United States Patent [19]

Yukata et al.

[11] 3,996,288
[45] Dec. 7, 1976

[54] METHOD OF PRODUCING ALDEHYDES BY HYDROFORMYLATION

[75] Inventors: Toshihide Yukata; Nobuyuki Yamakami; Masao Honma, all of Kawasaki; Yoshioki Komachiya, Yokohama; Hachiro Wakamatsu, Musashino; all of Japan

[73] Assignee: Ajinomoto Co., Inc., Tokyo, Japan

[22] Filed: May 22, 1974

[21] Appl. No.: 472,150

Related U.S. Application Data

[63] Continuation-in-part of Ser. No. 426,192, Dec. 19, 1973, abandoned.

[30] Foreign Application Priority Data

Dec. 23, 1972 Japan .................. 48-1254

[52] U.S. Cl. .................. 260/599; 260/604 HF; 260/518 R; 260/532; 260/534 C; 260/600 R; 260/602; 260/519
[51] Int. Cl.² .................. C07C 45/00
[58] Field of Search .......... 260/518 R, 599, 601 R, 260/604 HF, 532, 534 C

[56] References Cited

UNITED STATES PATENTS 3,766,266   10/1973   Wakomatsu et al. ...... 260/534 R X

OTHER PUBLICATIONS

Marko et al., Chem. Abs. vol. 60 (1964) 2847.
Wender, I. J.A.C.S. vol. 74 (1952), pp. 4079 to 4083.

Primary Examiner—Bernard Helfin
Attorney, Agent, or Firm—Hans Berman; Kurt Kelman

[57] ABSTRACT

When an alcohol or its hydrochloric or hydrobromic acid ester is held at 50° to 200° C and 10 to 500 atmospheres in the presence of hydrogen, carbon monoxide, the amide of a carboxylic acid, and a carbonylation catalyst, an aldehyde having one more carbon atom than the alcohol or ester is formed in a good yield. If the amide has at least one active hydrogen atom on its amide nitrogen, it further reacts with the aldehyde and carbon monoxide to form an N-acylamino acid by the reaction of U.S. Pat. No. 3,766,266.

4 Claims, No Drawings

METHOD OF PRODUCING ALDEHYDES BY HYDROFORMYLATION

This application is a continuation-in-part of the copending application Ser. No. 426,192, filed Dec. 19, 1973, and now abandoned.

This invention relates to the synthesis of aldehydes, and particularly to the preparation of aldehydes by hydroformylation.

It is known that nonyl aldehyde can be prepared by hydroformylation of octyl bromide (C.A. 60 [1964] 2847e). It is also known that alcohols can be converted to aldehydes in low yields by hydroformylation (J.A.C.S. 74 [1952] 4079). These known methods have not found industrial applications because they are not ecomonical.

It has now been found that alcohols and their hydrochloric and hydrobromic acid esters are converted to aldehydes having one additional carbon atom by hydroformylation in the presence of amides of carboxylic acids in good yields, and that the aldehydes are formed faster and at lower temperatures than in the known methods.

The exact function of the amide in the aldehyde formation is not yet known. The amide appears to participate in the reaction leading to the aldehyde, and limited tests indicate that an amide group present in the alcohol or ester employed as a starting material has an analogous effect. If the amide has an active hydrogen atom attached to its amide nitrogen, it reacts with the aldehyde formed and with available carbon monoxide according to the reaction disclosed in U.S. Pat. No. 3,766,266 to form an N-acyl-$\alpha$-amino acid.

Alcohols suitable for producing aldehydes according to the method of the invention include the alkanols, substituted alkanols, and saturated alicyclic alcohols, such as methanol, ethanol, propanol, butanol, isobutanol, $\beta$-cyanopropanol, $\beta$-methylmercaptoethanol, $\gamma,\gamma$-dimethoxybutanol, stearyl alcohol, lauryl alcohol, 2,4-dimethoxybenzyl alcohol, 2-hydroxymethylindole, cyclohexanol, and 4-methoxybenzyl alcohol. The hydrochloric and hydrobromic acid esters of these alcohols are representative of the esters suitable as starting materials for the aldehyde.

Best results are obtained with alcohols which contain groups acting as electron donors for the alcoholic hydroxyl group and have an absolute $pK_R+$ value of not less than $-18$ (for definitions, see D. Bethell et al, "Carbonium Ions", Academic Press, New York, 1967). Such alcohols include tert-butanol, anise alcohol, p-methoxybenzyl alcohol, veratryl alcohol, and p-hydroxybenzyl alcohol. Among the esters useful for this invention, those of benzyl alcohol with and without substituents in the benzene ring have greatest economic importance at this time.

Generally, the starting materials preferred for carrying out the method of this invention are alcohols of the formula

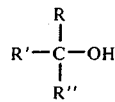

wherein R, R', R" may be hydrogen or lower alkyl, R also may be cycloalkyl having up to six carbon atoms, phenyl, chlorophenyl, monohydroxyphenyl, dihydroxyphenyl, mono-lower-alkoxyphenyl, or di-lower-alkoxyphenyl, lower alkyl and lower alkoxy having up to four carbon atoms, and the hydrochloric acid or hydrobromic acid esters of these alcohols.

The amides employed may be derived from any carboxylic acid, more specifically, any aliphatic, aromatic, alicyclic, or heterocyclic acid, and neither the number of carbon atoms nor the specific chemical structure are critical. Cyclic amides are effective as well. The wide range of suitable amides is illustrated by, but not limited to, formamide, acetamide, glycinamide, phthalylglycinamide, pyrrolidonecarboxylic acid, pyrrolidonecarboxamide, N-acetylmethionine amide, benzamide, propionamide, L- and DL-aspartic acid amide, the corresponding leucinamides, nicotinamide, and their N-monoalkyl and N-dialkyl derivatives such as N-methylformamide, N-dimethylformamide, N-diethylformamide, N-methylacetamide, and N-dimethylacetamide, to name merely those having the lowest number of carbon atoms and being most conveniently available.

The ratio of carbon monoxide to hydrogen in the reaction zone is not critical, but enough of each gas should be available to permit completion of the reaction if high yields are desired, that is, at least 1 mole carbon monoxide and 1 mole hydrogen per mole of the alcohol or halide ester in the aldehyde formation. The gases employed need not satisfy particular purity requirements although catalyst poisons will be avoided if the reaction is intended to continue over an extended period. Nitrogen, methane, and carbon dioxide, which are normal minor constituents of water gas, have no adverse effect on the reaction.

The catalysts for the purpose of the invention are those known to be useful in carbonylation and hydroformylation reactions, and include, as principal active element, one of the transition elements of Group VIII of the Periodic Table, namely the iron group metals (iron, cobalt and nickel) and the platinum group metals (ruthenium, rhodium, palladium, osmium, iridium and plantinum). For industrial purposes, catalysts including one of the elements of the iron group, particularly cobalt, are preferred. They may be supplied to the reaction zone as carbonyls, as metals, preferably finely dispersed, or as salts or complex compounds which form the carbonyls under the reaction conditions. Better results are often obtained when compounds containing phosphorus, nitrogen, oxygen, or halogen, which are known promoters for hydroformylation and carbonylation reactions, are also used as ligands.

When halide esters are used as starting materials, hydrogen halides are formed as by-products. In this event, the reaction is carried out more smoothly in the presence of acid acceptors, such as alkali metal or alkaline earth metal salts of weak acids, such as potassium acetate and magnesium propionate; organic bases, such as pyridine and triethylamine; and inorganic bases, such as ammonia and sodium hydroxide. The same effect can be obtained by using a reaction medium containing water because the amide initially present is partly decomposed by the water to an ammonium or amine salt of the corresponding carboxylic acid.

When an N-disubstituted amide is used for producing aldehydes in accordance with the method of this invention, an excess of amide is not required, and the amide is effective when present in the reaction mixure in a concentration of at least 0.01 mole per liter. When an amide having an active hydrogen atom on its amide nitrogen is used for producing an N-acyl-α-amino acid, the mole ratio of the amide to the alcohol or halide is not critical, but an excess of the amide tends to increase the yield.

The amount of catalyst employed varies with the metal used, but is is usually within the range of 1 to 0.01 mole per mole of the product formed. The reaction temperature is not critical, but it is preferably between 50° and 200 ° C. The reaction pressure is usually within the range of 10 to 500 atmospheres, as in amy carbonylation and hydroformylation reactions.

The reaction is preferably carried out in a system which includes a solvent as a diluent. The solvents normally employed in carbonylaton and hydroformylaton reactions are also effective for this invention. When a halide ester is used as a starting material, especially together with a neutralizing agent (an acid acceptor), a mixture of water and an organic solvent sparingly soluble in cold water is preferred as a reaction medium for convenient operation and good yield. Suitable organic solvents include hydrocarbons such as toluene, benzene and hexane; ketones such as methyl isobutyl ketone and methyl ethyl ketone; ethers such as diethyl ether and dibutyl ether; nitriles such as butyronitrile and benzonitrile; and esters such as ethyl acetate and butyl acetate.

To recover the reaction product from the reaction mixture, it is normally preferred first to remove the catalyst and the solvent, if any. The recovery methods will be obvious to those skilled in the art from the nature of the specific product to be recovered.

The aldehydes prepared by the method of this invention are well-known useful chemicals, while the N-acyl derivatives may be hydrolyzed in an obvious manner to yield amino acids.

The following Examples further illustrate this invention. In every Example, a 100 ml stainless steel pressure vessel equipped with an electromagnetic stirrer was used as a reactor.

EXAMPLE 1

6.4 g (50 Millimole) benzyl chloride, 4.5. g dicobalt octacarbonyl, 3.65 g (50 millimole) dimethylformamide, and 50 ml acetone were placed in the reactor which was then charged to a gas pressure of 140 kg/cm$^2$ with a mixture of equal volumes of carbon monoxide and hydrogen.

The contents of the reactor were stirred at 120° C for 20 minutes. The reactor was then cooled, and a blue liquid was poured from the reactor. From analysis of a sample by gas chromatography, the reaction mixture was found to contain 26.1 millimoles of phenylacetaldehyde, which corresponds to a 52.2% yield based on the benzyl chloride employed.

For comparison purposes, the above procedure was repeated without dimethylformamide, but the reaction period was extended to 2 hours. The reaction mixture was found to contain only 8.45 millimoles of phenylacetaldehyde, which corresponds to a 16.9% yield based on the benzyl chloride employed.

EXAMPLE 2

6.4 g (50 Millimole) benzyl chloride, 2 g dicobalt octacarbonyl, 3.65 g (50 millimole) dimethylformamide, 3.15 g sodium bicarbonate, 32 ml methyl isobutyl ketone, and 9 ml water were placed in the reactor which was then charged to a gas pressure of 200 kg/cm$^2$ with a 1:1 mixture of carbon monoxide and hydrogen.

The contents of the reactor were stirred at 110° C for 30 minutes, whereby 12 millimoles of the gas were absorbed. The reactor was then cooled, and the reaction mixture was poured from the reactor. The mixture consisted of 40 ml of a yellowish-brown upper layer and 11 ml of a reddish-purple lower layer. The amounts of phenylacetaldehyde in the upper and lower layers were found by gas chromatography to be 28 and 2 millimole respectively, which corresponds to a 60% yield based on the benzyl chloride employed.

EXAMPLE 3

8.1 g (50 millimole) p-chlorobenzyl chloride, 4 g dicobalt octacarbonyl, 1.9 g (20 millimole) N-methylpyrrolidone, and 50 ml dioxane were placed in the reactor, which was then charged to a gas pressure of 200 kg/cm$^2$ with a 1:1 mixture of carbon monoxide and hydrogen. The contents of the reactor were stirred at 120° for 30 minutes, the reactor was cooled, and a blue liquid was poured therefrom.

A sample of the reaction mixture was analyzed by gas chromatography, and the whole reaction mixture was found to contain 24.3 millimoles of p-chlorophenylacetaldehyde, which corresponds to a 48.6% yield based on the p-chlorobenzyl chloride employed.

EXAMPLE 4

6.4 g (50 Millimole) benzyl chloride, 30 g (50 millimole) acetamide, 4 g dicobalt octacarbonyl, and 50 ml ethyl acetate were placed in the reactor which was then charged to a gas pressure of 200 kg/cm$^2$ with a 1:1 mixture of carbon monoxide and hydrogen.

The contents of the reactor were stirred at 110° C for 20 minutes, whereby 30 millimoles gas were absorbed. The reactor was cooled, and a blue liquid was poured from the reactor. It was found to contain 32 milliequivalents of a carboxylic acid.

From a sample of the reaction mixture, the carboxylic acid was adsorbed on an anion exchange resin (Amberlite-4B), and the material recovered by elution was identified as N-acetylphenylalanine by elementary analysis, melting point, and infrared and mass spectra.

Another sample of the reaction mixture was treated with diazomethane to convert the N-acetylphenylalanine therein to N-acetylphenylalanine methyl ester. The concentration of the ester was determined by gas chromatography, and the reaction mixture was calculated to contain 28.4 millimoles of N-acetylphenylalanine which corresponds to a 56.8% yield based on the benzyl chloride employed.

EXAMPLE 5

6.4 g (50 Millimole) benzyl chloride, 5.9 g (100 millimole) acetamide, 4 g dicobalt octacarbonyl, 47.5 ml acetone, and 2.5 ml water were placed in the reactor which was then charged to a gas pressure of 200 kg/cm$^2$ with a mixture of one volume carbon monoxide and 2 volumes hydrogen.

The contents of the reactor were stirred at 120° C for 20 minutes, whereby 67.6 millimoles of the gas were absorbed. The reactor was cooled, and a blue liquid was poured from the reactor. It was found to contain 40 milliequivalents of a carboxylic acid.

From a sample of the reaction mixture, the carboxylic acid was adsorbed on an anion exchange resin (Amberlite-4B), and the material recovered by elution was identified as N-acetylphenylalanine by elementary analysis, melting point, and infrared and mass spectra.

The amount of N-acetylphenylalanine in the reaction mixture was determined by gas chromatography of a sample after treatment with diazomethane to be 38.6 millimoles, which corresponds to a 77.2% yield based on the benzyl chloride employed.

EXAMPLE 6

6.4 g (50 Millimole) benzyl chloride, 5.9 g (100 millimole acetamide, 1 g dicobalt octacarbonyl, 50 ml acetone, and 0.9 g water were placed in the reactor which was then charged to a gas pressure of 400 kg/cm$^2$ with a 1:1 mixture of carbon monoxide and hydrogen.

The contents of the reactor were stirred at 110° C for 1 hour. The reaction mixture was worked up as in Example 4. The N-acetylphenylalanine waas found to amount to 30.8 millimoles, which corresponds to a 61.6% yield based on the benzyl chloride employed.

EXAMPLE 7

6.4 g (50 Millimole) benzyl chloride, 2.0 g dicobalt octacarbonyl, 3.69 g (67.5 millimole) acetamide, 3.15 g sodium bicarbonate, 30 ml methyl isobutyl ketone, and 10 ml water were placed in the reactor, which was then charged to a gas pressure of 200 kg/cm$^2$ with a mixture of one volume carbon monoxide and one volume hydrogen.

The contents of the reactor were stirred at 110° C for 30 minutes, whereby 38 millimoles of the gas were absorbed. The reactor was then cooled, and the reaction mixture was poured from the reactor. The mixture consisted of 40 ml of a yellowish-brown upper layer and 10 ml of a reddish-purple lower layer.

Air was bubbled through the mixture for 30 minutes to decompose the catalyst, and a sample of each layer was analyzed by gas chromatography after treatment with diazomethane. The N-acetylphenylalanine in the upper and lower layers respectively amounted to 32 millimoles and 2.7 millimoles, which corresponds to a 69.4% yield based on the benzyl chloride employed.

EXAMPLE 8

6.4 g (50 Millimole) benzyl chloride, 12.1 g (100 millimole) benzamide, 4 g dicobalt octacarbonyl, and 50 ml ethyl acetate were placed in the reactor which was then charged to a gas pressue of 200 kg/cm$^2$ with a mixture of 2 volumes carbon monoxide and one volume hydrogen.

The contents of the reactor were stirred at 130° C for 30 minutes, whereby 50 millimoles of the gas were absorbed. The reactor was cooled, and a blue liquid was poured from the reactor. It was found to contain 36 milliequivalents of a carboxylic acid.

From a sample of the reaction mixture, the carboxylic acid was adsorbed on an anion exchange resin (Amberlite-4B), and the material recovered by elution was identified as N-benzoylphenylalanine by elementary analysis, melting point, and infrared and mass spectra. The N-benzoylphenylalanine in another sample of the reaction mixture was determined by gas chromatography after treatment with diazomethane. The whole reaction mixture was found to contain 32.5 millimoles of N-benzoylphenylalanine, which corresponds to a 65% yield based on the benzyl chloride employed.

EXAMPLE 9

6.4 g (50 Millimole) benzyl chloride, 6.3 g (100 millimole) N-methylacetamide, 1 g dicobalt octacarbonyl, 40 ml methyl isobutyl ketone, and 10 ml water were placed in the reactor which was then charged to a gas pressure of 280 kg/cm$^2$ with a 1:1 mixture of carbon monoxide and hydrogen.

The contents of the reactor were stirred at 80° C for 100 minutes. The reactor was cooled, and the reaction mixture was poured from the reactor. It consisted of 36 ml of a faintly yellowish-green upper layer and 13 ml of a purple lower layer.

The whole reaction mixture was diluted to 100 ml with methanole. The resulting solution was analyzed by gas chromatography and was found to contain 30 millimoles of N-methylacetylphenylalanine, which corresponds to a 60% yield based on the benzyl chloride employed.

EXAMPLE 10

13.8 g (100 Millimole) anise alcohol, 0.6 g dicobalt octacarbonyl, 3.65 g (50 millimole) dimethylformamide, and 50 ml ethyl acetate were placed in the reactor which was then charged to a gas pressure of 200 kg/cm$^2$ with a 1:1 mixture of carbon monoxide and hydrogen.

The contents of the reactor were stirred at 120° C for 30 minutes, whereby 160 millimoles of the gas were absorbed. The reactor was cooled, and a red liquid was poured from the reactor. It was found to contain 70 millimoles of a carbonyl compound by reaction with hydroxylamine hydrochloride.

A sample of the mixture was analyzed by gas chromatograpy, and the whole reaction mixture was found to contain 55 millimoles p-methoxyphenylacetaldehyde, which corresponds to a 55% yield based on the anise alcohol employed.

EXAMPLE 11

6.9 g (50 Millimole) anise alcohol, 0.4 g dicobalt octacarbonyl, 2.1 g (25 millimole) dimethylacetamide, and 50 ml dioxane were placed in the reactor, which was then charged to a gas pressure of 200 kg/cm$^2$ with a 1:1 mixture of carbon monoxide and hydrogen.

The contents of the reactor were stirred at 110° C for 20 minutes, whereby 80 millimoles gas were absorbed. The reactor was cooled, and a red liquid was poured therefrom. It was found to contain 43 millimoles of a carbonyl compound.

An aliquot of the mixture was analyzed by gas chromatography, and the whole reaction mixture was found to contain 32 millimoles of p-methoxyphenylacetaldehyde, which corresponds to a 64% yield based on the anise alcohol employed.

EXAMPLE 12

8.4 g (50 Millimole) veratryl alcohol, 3.0 g (50 millimole) acetamide, 0.6 g dicobalt octacarbonyl, and 50 ml acetone were placed in the reactor which was then charged to a gas pressure of 200 kg/cm$^2$ with a 2:1 mixture of carbon monoxide and hydrogen.

The contents of the reactor was stirred at 110° C for 50 minutes, whereby 101.3 millimoles of the gas were absorbed. The reactor was cooled, and a faintly yellow liquid was poured therefrom. It was found to contain 26.9 milliequivalents of a carboxylic acid.

From a sample of the mixture, the carboxylic acid was recovered by means of an anion exchange resin (Amberlite-4B) and identified as N-acetylveratrylglycine by elementary analysis, melting point, and infrared and mass spectra. The N-acetylveratrylglycine was determined by gas chromatography after treatment with diazomethane to amount to 23.4 millimoles, which corresponds to a 46.8% yield based on the veratryl alcohol employed.

EXAMPLE 13

6.9 g (50 Millimole) anise alcohol, 2.95 g (50 millimole) acetamide, 0.6 g dicobalt octacarbonyl, and 50 ml ethyl acetate were placed in the reactor, which was then charged to a gas pressure of 200 kg/cm$^2$ with a 2:1 mixture of carbon monoxide and hydrogen. The contents of the reactor were stirred at 120° C for 30 minutes, whereby 110 millimoles of the gas were absorbed. The reactor was cooled, and a faintly yellow, clear liquid was poured therefrom. It was found to contain 32 milliequivalents of a carboxylic acid.

From a sample, the carboxylic acid was recovered by means of an anion exchange resin and identified as N-acetyl-O-methyltyrosine by elementary analysis, melting point, and infrared and NMR spectra. The N-acetyl-O-methyltyrosine was determined by gas chromatography after treatment with diazomethane to amount to 25 millimoles, which corresponds to a 50% yield based on the anise alcohol employed.

EXAMPLE 14

6.2 g (50 Millimole) p-hydroxybenzyl alcohol, 2.95 g (50 millimole) acetamide, 0.6 g dicobalt octacarbonyl, and 50 ml dioxane were placed in the reactor, which was charged to a gas pressure of 210 kg/cm$^2$ with a 2:1 mixture of carbon monoxide and hydrogen. The contents of the reactor were stirred at 120° for 30 minutes, whereby 103 millimoles of the gas were absorbed. The reactor was cooled, and a faintly yellow, clear liquid was poured therefrom. It was found to contain 32 millimoles of a carboxylic acid.

From a sample of the mixture, the carboxylic acid was recovered by means of an anion exchange resin (Amberlite-4B) and identified as N-acetyltyrosine by elementary analysis, melting point, and infrared and NMR spectra.

An aliquot of the reaction mixture was refluxed with 6N hydrochloric acid to hydrolyze the N-acetyltyrosine to tyrosine. The tyrosine content of the hydrolyzate was determined by means of an amino acid analyzer. The whole reaction mixture was found to contain 16.5 millimoles of N-acetyltyrosine, which corresponds to a 33% yield based on the p-hydroxybenzyl alcohol employed.

EXAMPLE 15

1.6 g (50 Millimole) methanol, 5.9 g (100 millimole) acetamide, 1 g dicobalt octacarbonyl, 1.6 g potassium iodide, and 50 ml acetone were placed in the reactor, which was then charged to a gas pressure of 200 kg/cm$^2$ with a 2:1 mixture of carbon monoxide and hydrogen. The contents of the reactor were stirred at 140° C for 120 minutes, whereby 110 millimoles of the gas were absorbed. The reactor was cooled, and a faintly brown liquid was poured therefrom.

An aliquot of the reaction mixture was analyzed in the same manner as in Example 4, and the reaction mixture was found to contain 14.2 millimole N-acetylalanine, which corresponds to a 28.4% yield based on the methanol employed.

EXAMPLE 16

3.7 g (50 Millimole) tert-butyl alcohol, 2.95 g (50 millimole) acetamide, 0.6 g dicobalt octacarbonyl, and 50 ml ethyl acetate were placed in the reactor, which was then charged to a gas pressure of 200 kg/cm$^2$ with a 2:1 mixture of carbon monoxide and hydrogen. The contents of the reactor were stirred at 150° C for 60 minutes, whereby 100 millimoles of the gas were absorbed. The reactor was cooled and a red, turbid liquid was poured therefrom. It was found to contain 25.7 milliequivalents of a carboxylic acid.

A sample of the mixture was analyzed by a combined gas chromatograph and mass spectrometer, and it was found that N-acetylleucine and N-acetyl-3-methylvaline had been produced. The amounts of N-acetylleucine and N-acetyl-3-methylvaline were respectively found to be 11.5 millimoles (23.0% yield based on the alcohol) and 1.8 millimoles (3.6% yield) by gas chromatograpy.

EXAMPLE 17

In a procedure similar to that described in Example 13, 10.5 g (50 millimole) veratryl alcohol acetate was employed instead of the anise alcohol. The resulting reaction mixture was reddish-brown and turbid, and was found to contain 45 milliequivalents of a carboxylic acid.

A sample of the mixture was worked up as in Example 13 after removal of the acetic acid formed. The recovered carboxylic acid was identified as N-acetylveratrylglycine by elementary analysis, melting point, and infrared and mass spectra. The N-acetylveratrylglycine was found by gas chromatography after treatment with diazomethane to amount to 15 millimoles which corresponds to a 30% yield based on the veratryl alcohol acetate employed.

EXAMPLE 18

6.4 Benzyl chloride (50 millimole, 8.85 g acetamide (150 millimole), 1.0 g dicobalt octacarbonyl, 33 ml methyl isobutyl ketone, and 10 ml water were placed in the reactor which was then charged with a 1:1 mixture of carbon monoxide and hydrogen to a pressure of 260 kg/cm$^2$. After 30 minutes stirring at 100° C, the reactor was cooled to ambient temperature, and the reaction mixure discharged from the reactor was diluted to 100 ml with methanol, whereby a homogeneous solution was formed.

The residual benzyl chloride and the phenylacetaldehyde formed were determined by gas chromatography of a sample, and another sample was reacted with diazomethane and analyzed for N-acetylphenylalanine methyl ester. It was found that 97% of the benzyl chloride originally present had been consumed, and that 25% of the benzyl chloride had been converted to phenylacetaldehyde while 56% was converted to N-acetylphenylalanine.

When the reaction time was extended to 50 minutes, 99% of the benzyl chloride was consumed, less than 2% was converted to phenylacetaldehyde, and 79% of the benzyl chloride was converted to N-acetylphenylalanine.

Comparison of the two sets of results indicates that phenylacetaldehyde was the primary product which then reacted with the acetamide present.

In a further comparison test, acetamide was omitted from the reaction mixture which was held at 100° C and 260 kg/cm$^2$ for 30 minutes. Only 30% of the benzyl chloride was consumed, and only 5% of the benzyl chloride was converted to phenylacetaldehyde. No N-acetylphenylalanine could be found.

EXAMPLE 19

4.3 g Methylcyclopropylcarbinol (50 millimole), 3.0 g acetamide (50 millimole), 0.6 g dicobalt octacarbonyl, and 45 ml acetone were placed in the reactor which was then charged to 197 kg/cm² with a 1:1 mixture of carbon monoxide and hydrogen, and held at 140° C with stirring for 60 minutes, whereby 131 millimoles of the gas were absorbed. After cooling, a brown liquid was poured from the reactor. 28 Millimoles N-acetyl-2-amino-3cyclopropylbutyric acid was found in the reaction mixture for a yield of 56% based on the alcohol initially employed.

EXAMPLE 20

6.9 g Isobutyl bromide (50 millimole), 5.9 g acetamide (100 millimole), 1 g dicobalt octacarbonyl (2.94 millimole), and 50 ml ethyl acetate were placed in the reactor together with a 2:1 mixture of carbon monoxide and hydrogen at 200 kg/cm². After stirring at 140° C for 190 minutes, 38.6 millimole gas was absorbed, and a blue reaction mixture was discharged from the reactor after cooling.

It contained 30 milliequivalents of a carboxylic acid, and 14.0 millimoles N-acetylleucine (28% yield based on the isobutyl bromide employed) were found in the mixture by the methods described above.

What is claimed is:

1. A method of preparing phenylacetaldehyde which comprises holding a reaction mixture including hydrogen, carbon monoxide, an amide of a carboxylic acid and benzyl chloride at 50°C to 200°C and at a pressure between 10 and 500 atmospheres in the presence of a carbonylation catalyst until said aldehyde is formed, the concentration of said amide in said mixture being at least 0.01 mole per liter, and said carbonylation catalyst containing as the principal active agent, a transition element of Group VIII of the Periodic Table.

2. A method as set forth in claim 1, wherein said principal active agent is cobalt.

3. A method as set forth in claim 1, wherein said amide is acetamide, and said catalyst is dicobalt octacarbonyl.

4. A method as set forth in claim 1, wherein the amount of said catalyst is between 1 and 0.01 mole per mole of said aldehyde.

* * * * *